United States Patent [19]

Patwardhan

[11] Patent Number: 5,494,668
[45] Date of Patent: Feb. 27, 1996

[54] METHOD OF TREATING MUSCULOSKELETAL DISEASE AND A NOVEL COMPOSITION THEREFOR

[76] Inventor: Bhushan Patwardhan, 1471 Shukarwar Peth, Bhaumaharaj Bol, Poona 411 002, Ind.

[21] Appl. No.: 273,189

[22] Filed: Jul. 11, 1994

[51] Int. Cl.⁶ .................................................. A61K 35/78
[52] U.S. Cl. ...................... 424/195.1; 514/825; 514/886; 514/925
[58] Field of Search .................. 424/195.1; 514/825, 514/886, 925

[56] References Cited

U.S. PATENT DOCUMENTS

| | | | |
|---|---|---|---|
| 4,324,785 | 4/1982 | Stevens | 424/195.1 |
| 4,906,471 | 7/1990 | Liu | 424/195.1 |
| 5,064,823 | 11/1991 | Lee et al. | 514/198 |
| 5,120,538 | 6/1992 | Oie | 424/195.1 |

*Primary Examiner*—John W. Rollins

[57] ABSTRACT

A method of treating degenerative musculoskeletal diseases such as rheumatoid arthritis and osteoarthritis in an animal, typically a human, comprises administering to the animal, typically enterally, in a convenient dosage form, a therapeutically effective amount of the beneficiated extracts of the plants ASHWAGANDHA (*Withania somnifera*), SALLAI GUGGUL (*Boswellia serrata*), TURMERIC (*Curcuma longa*), and GINGER (*Zingiber officinale*) in a predetermined proportion relative to each other with or without other biologically active inorganic ingredients, such as zinc sulphate. The beneficiated plant extracts are made in accordance with a novel process which is also disclosed.

12 Claims, 3 Drawing Sheets

METHOD OF TREATING MUSCULOSKELETAL DISEASE AND A NOVEL COMPOSITION THEREFOR

FIELD OF INVENTION

The present invention is directed to provide a synergistic composition for immunomodulatory activity with special references to rheumatic diseases, immunodeficiency diseases and various forms of degenerative musculoskeletal diseases such as rheumatoid arthritis and osteoarthritis.

DESCRIPTION OF THE BACKGROUND ACTIVITY OF THE ART

Immunology plays an important role in understanding and diagnosis of disease and further it is the most rapidly developing area of biomedical research for the prevention and treatment of a wide range of disorders. Arthritis. ulcerative colitis, asthma, allergic reactions, parasitic and infectious diseases are now primarily considered to be immunological disorders. Immune mechanisms are also involved in a variety of other diseases such as diabetes mellitus, cancer, myocardial diseases, cirrhosis and atherosclerosis.

The modulation of immune response by using a variety of agents in order to alleviate the disease has been of interest since many years and the first authentic experimental report on immunomodulation was made by Lazarev in 1947 in which he effectively demonstrated the capacity of diabazol to increase non-specific resistance. This activity was termed as adaptogenic.

The non-specific immunity is provided by granulocytes, macrophages, natural killer cells, complement and properdin, and the various effector substances including interleukins, tumour necrosis factor, interferons, lysozymes, prostaglandins, oxygen radicals and other mediators. From the evolutionary angle, this non-specific immunity is more primitive, because it responds immediately without any initial latent period and it does not have immunological memory.

The inflammatory and allergic manifestations in the living cell are thought to be the direct cause of hyperactivity of immune function entities in non-specific immunity, whereas the the suppression or deficiency of immune functions are the result of hypoactivity. The functioning and efficiency of non-specific immunity may be influenced by many exogenous and endogeneous factors like physical and psychological stress, hormonal imbalance, pharmaceuticals and the like.

'Immunomodulation' is any procedure which can alter non specific immunity by interfering with its functioning. If it results in enhancement of immune reactions, it results in immunostimulation and primarily implies stimulation of the non specific immunity, that is stimulation of the function and efficiency of granulocytes, macrophages, natural killer cells, complement and properdin, and the various effector substances including interleukins, tumour necrosis factor, interferons, lysozymes prostaglandins, oxygen radicals and other mediators. Immunosuppression mainly implies reduced resistance against infections and stress and may be due to environmental or chemotherapeutic factors.

Immunostimulation and immunosuppression both need to be addressed in order to regulate normal immunological functioning. Hence, immunostimulating and immunosuppressing agents both have their own standing. There are a variety of known immunosuppressing agents, for instance cyclosporin, however few immunostimulating agents are available. Apart from specific stimulative or suppressive activity, it is believed that certain agents of plant origin have the activity to normalize or modulate pathophysiological processes in the underlying immune response and hence the term immunomodulation or immunomodulatory agents are used for these agents. This activity is believed to be dose dependant as can be seen from the immunostimulation at low dilutions of many immunosuppressants.

Most of the chemical agents known to have effect on the immune system are immunosuppressants and cytotoxic agents. For instance, Azathioprine inhibits DNA synthesis, Cyclophosphamide is relatively selective for lymphoid tissue. Cyclosporin A has applications in organ transplantations, thiocarbomate has direct cytotoxic effects. Many chemotherapeutic agents available today are basically immunosuppressants, most of them are cytotoxic and exert a variety of side effects. Further, the metabolism and clinical safety of these agents has also not been clearly established. On the other hand there are reasons to believe that plant extracts having pharmacologically and biologically activity can serve as a good source for newer immunostimulants. Brekman et al have studied a large number of folk medicines from different parts of the world and these are reviewed in the Annual Review of Pharmacology, 1969.

Plants having pharmacological and biological activity have been the basis of treatment of human diseases from time immemorial. Every country in the world has lists of herbal remedies for the treatment of diseases and various human conditions. The foundations of the modern drug industry are practically based on the inventions of active compounds from plants which have been developed further synthetically to obtain more suitable analogues. For example the isolation of morphine from opium poppy by Fredric Serterner, Quinine from the cinchona tree, cocaine from the leaves of Coca shrubs, and a host of drugs such as atropine, curate, digoxin, reserpine and the like.

There are reasons to believe that most of the plants used in the past for critical research for developing new drugs are mainly of a poisonous nature. This, it is believed, has happened because of two primary reasons. Firstly, the lack of knowledge in selecting correct plants having medical activity and not being poisonous and lack of know-how of the required technology in drug research. It is relatively easy to identify a poisonous plant in the forests. It is extremely difficult to identify non-poisonous plants having truly medicinal properties. To determine the poisonous character of a plant a few generation studies are often adequate. The identification of medicinal activity of a plant needs studies spread over a large number of generations.

In India, Ayurveda, has carried out these studies for many generations and has recorded the medicinal uses of specific plants for over 5000 years or even more. These records are valuable, since effectively these medicines have been tested for centuries on millions of people. It is suggested that the plant extracts identified in the present invention with potential immunomodulatory activity along with other supportive activity will provide short and long term benefits to patients having immunopathological disorders such as rheumatic diseases and degenerative diseases of the musculoskeletal system, such as osteoarthritis.

This invention relates to a process for obtaining a pharmacologically or biologically active plant extract substantially as it occurs in its natural state suitable for converting in a convenient administrable dosage form.

Use of pharmacologically or biologically active plant extracts is well-known. It is also known that the biologically or pharmacologically active compounds can be isolated and purified from the plant extract to obtain therapeutic compositions.

According to drug-receptor theory, the compatibility of the structure of a drug with the receptor, is considered to be most important for determining the maximal or optimal activity of any drug. Following this principle, most of the modern drugs have been invented by synthetic modification of active molecules from natural or other sources by following Hanch Analysis and QSAR studies. Such drug-receptor interaction can also be studied non on CADD by artificial simulation and thus discovering the best possible structure for maximum activity. In this exercise, a large number of structural analogues are needed to be synthesized and further tested for pharmacologically or biologically activity or bio-activity. The main purpose of this exercise is to determine the most suitable structure for maximum activity.

Most drugs which have developed from such exercises are not completely compatible with the requirements of the receptor site. Thus they have limitations in therapeutic management and simultaneously exhibit toxic effects. Synthetic synthesis and purification processes have not been able to emulate the pharmacologically or biologically activity of natural substances such as atropine, digitalis, reserpine, nicotine and the like.

Naturally occurring plant material contain a series of closely-related compounds produced naturally via biological and biochemical reactions. The plant is capable of producing a wide range of analogues at least one of which possesses the desired receptor compatibility. However, the related compounds appear to exercise a synergistic effect on the pharmacologically or biologically activity of the compatible compound and at the same time suppress toxic effects. However, a major drawback in using plant material in its crude form, is that the dosages required of such material, to be therapeutically beneficial, are quite high, sometimes even upto 10 gms a day or more. Such quantities cannot be conveniently converted into suitable dosage forms.

This invention, therefore, seeks to disclose a process for obtaining a pharmacologically or biologically active plant extract substantially as it occurs in its natural state suitable for converting in a convenient administrable dosage form.

The process according to this invention, seeks to provide a beneficiated plant extract, in which the plant extract comprises all pharmacologically or biologically active chemicals in their original natural state and proportions.

Thereby, the advantage of naturally occurring series and analogues of compounds is achieved without compromising the overall effects of these compounds.

This invention specifically relates to a pharmaceutical synergistic composition for the treatment of rheumatic diseases and degenerative diseases of the musculo-skeletal system. Note specifically for the treatment of rheumatoid arthritis and osteoarthritis.

Arthritis is a common progressive disease of various etiologies. Common symptoms include pain and inflammation of one or more joints.

Rheumatoid arthritis is a chronic syndrome characterised by non-specific usually symmetric inflammation of the peripheral joints, potentially resulting in progressive destruction of articular and periarticular structures leading to deformity. There is a wide spectrum of disease severity but many patients run a course of intermittent relapses and remissions with an overall pattern of slowly progressive joint destruction and deformity. Persistent inflammation produces symptoms and damages tissue causing loss of cartilage, erosion of bone matter and subluxation of joint. This results in a high degree of morbidity resulting in disturbed daily life of the patient.

The etiology of this debilitating disease is unknown, however it is considered to be immmuno pathalogical in origin. It is believed to be the result of the presence of a relevant antigen to an immunogenetically susceptible host. Presence of rheumatoid factor in blood, increase in the erythrocyte sedimentation rate and induced radiological changes are used for classification and correct diagnosis.

Present treatment of Rheumatoid Arthritis includes first line drugs for control of pain and inflammation classified as non-steroidal, anti-inflammatory drugs (NSAIDS). Secondary treatment include corticosteroids, slow acting antirheumatic drugs (SAARDS) or disease modifying (DM) drugs include penicillinamine like drugs such as cyclophosphamide, methotrexate, gold salts, azothioprine, levamisole and the like. All these drugs have severe side effects and most of them are cytotoxic.

Out of the aforesaid drugs, only levamisole can be categorised as immunostimulatory and has been reported to reduce rheumatoid factor titers.

The drugs used at present have limited advantages and their effects mainly of short term duration and there are many disadvantages in the use of these drugs over extended periods of time. Further the drugs used at present are costly and have low benefit-risk ratio. The ideal compound to modify the progress of the disease has not yet been found hithertofore.

The usefulness of immunmodulatory drugs in the treatment rheumatoid arthritis is based on the following evidences for immunopathalogical disorders in this disease. The disease is primarily an inflammation of joints in which the synovium is expanded by an infiltrate of cells—Lymphocytes; plasma cells and a variety of other cells, mostly mononuclear cells; the joint fluid is rich in polymorphoneuclear leucocytes; and the cartilage is destroyed by the advancing edge of synovial connective tissue called panus. Rheumatoid Arthritis is therefore a chronic multisystem disease of unknown etiology characterized chiefly by persistent inflammatory synovitis, usually involving peripheral joints in a symmetrical fashion. Cartilaginous destruction, bony erosions, and joint deformation are hallmarks of persistent synovial inflammation. Pathogenesis is not well understood; synovial hyperboles and hypertrophy, lymphocytic infiltration of synovial tissue, joint infiltration by neutrophils, protease release, and chondrocyte activation occur. Free radical damage is also believed to be the important factor in its pathophysiology.

The clinical manifestations include symmetrical polyarthritis of peripheral joints with pain, tenderness, and swelling of affected joints; morning stiffness is common; PIP and MCP joints frequently involved; joint deformities may develop after persistent inflammation. Extra-articular manifestations include rheumatoid nodules, rheumatoid vasculitis, pleuropulmonary inflammations, scleritis, sicca syndrome, Felty's syndrome (splenomegaly and neutropenia) osteoporosis.

It is believed that rheumatoid arthritis results from the presentation of a relevant antigen to an immunogenetically susceptible host. The antigens that could potentially initiate an immune response that results in rheumatoid arthritis might be endogeneous or exogeneous. Possible endogeneous antigens include collagen, mucopolysaccharides and rheumatoid factors. Exogeneous antigens include mycoplasms, mycobacteria, spirochytes and viruses. The Epstein-Barr virus has received the most attention as a possible cause of rheumatoid arthritis.

This invention also relates to a process of obtaining beneficiated biologically active extracts obtained from the following naturally occurring plant species: ASHWAGANDHA (*Withania somnifera*), SALLAI GUGGUL (*Boswellia serrata*), TURMERIC (*Curcuma longa*), GINGER (*Zingiber officinale*) for use in a composition for the treatment of rheumatoid arthritis and osteoarthritis.

Ashwagandha—*Withania somnifera* (Solanaceae)

This plant is native to the Indian sub-continent and has been fairly well studied for its chemistry, pharmacology and clinical efficacy. (Sharma K. and Dandia P. C. 1992, Indian Drugs 29 (6) 247–255). Chemical constituents include alkaloids (withanine, withasomnin,) and steroidal glycosides (sitoindosides and withanolides). (FIG. 1 of the accompanying drawing). (Lavie D.; Phytochemistry, 1975, 14, 189) Withaferin A is the most important of the withanolides.

Sitoindosides and Withanolides together are mainly responsible for the biological activity of Ashwagandha which could be attributed to its usefulness in a wide variety of pathological states. Further Ashwagandha has demonstrated antipyretic, analgesic, antiinflammatory, antiarthritic, anabolic, hepatoprotective and antitumor activities.

There are both animal and clinical experimental evidence for potential antiarthritic and antirheumatic activity of Ashwagandha. (Anabalgen K. and Sadique J. Indian Journal of Experimental Biology 1981, 19; 245–249; Bactor N. P. et al Journal of Research in Indian Medicine 1971 5(2) 72,) It has fairly potent analgesic and antiinflammatory properties. Ashwagandha suppresses effectively arthritic syndrome without any toxic effect. Unlike hydrocortisone which causes weight loss, animals treated with Ashwagandha showed weight gain even in arthritic syndrome. Withanolides have been found to be better than hydrocortisone in its edema-inhibiting activity while suppression of granulation-tissue formation was similar to hydrocortisone. (Budhiraja and Sudhir S., Journal of Scientific and Industrial Research, 1987, 46, 488–491). Acute phase Reactants (APR) of the blood monitored by crossed immune electrophoresis reveals changes in the concentration of many serum proteins by drug treatment. Several compounds in Ashwagandha particularly withanolides are considered to interact with the liver protein synthetic machinery and thus influence many modular proteins which is unlike phenylbutazone. NSAIDs have none or very weak influence on APR, which is contrary to SAIDs. A bulk of evidence manifests an apparent antiinflammatory and anti arthritic activity of the plant against various models of inflammation in carageenan, Cotton pellet granuloma and adjuvant arthritis where long term administration of Ashwagandha has shown significant radiographical changes. (Begum and Sadique, 1988 Indian Journal of Experimental Biology 26 (11) 877). Long term effects of Ashwagandha in adjuvant arthritis have shown modulating effect on serum levels of trace elements viz, Cu(ions), Zn(ions) and Fe(ions). (Sadiq J. et al, Acta Pharmacology and Toxicology 1986, 59 (7) 406). A possible mechanism of antiinflammatory activity has been proposed. Further, long term administration exerts anabolic activity and is devoid of any toxic effect even after 8 months daily administration. (Sharma S.; et al Indian Drugs 1986 25(5), 155–157). Inspite of bulk of experimental data on usefulness of Ashwagandha as analgesic, antiinflammatory, antiarthritic, antirheumatic and immunomodulatory properties, very few systematic clinical trials have been conducted. Bactor et.al. studied 118 cases of arthropathies including 78 of rheumatoid arthritis and showed that Ashwagandha is useful in acute rheumatoid arthritis. Chronic cases were improved and significant fall in ESR was noted. No side effects were observed during the treatment and follow-up studies upto six months in the doses ranging from 4–6 g/day.

Thus Ashwagandha (*Withania somnifera*) contains a variety of chemicals including alkaloids (withanine, withasomnin) and steroidal lactones and glycosides also called as withanoloids and sitoindosides. The chemicals from the extract of Ashwagandha (*Withania somnifera*) has analgesic, mildly sedative, anti-inflammatory and anabolic activities. They also have immunomodulatory activity. Several compounds, particularly withanoloids are believed to interact with the liver protein synthesis activity and thus influence many modular proteins. Long term administration has shown beneficial radiological changes, reduction in erythrocyte sedimentation rate and acute phase symptoms including C-reactivity proteins. Ashwagandha (when given in the predetermined dosages in the composition), will not cause any severe side effects or undesired effects. Given alone, Ashwagandha (*Withania Somnifera*) has limited long term benefits.

Sallai Guggul (*Boswellia serrata*) (Bursaceae) an oleo-gum-resin obtained from trees of Sallai Guggul as a stem exudate. Sallai Guggul contains Beta boswellic acid which is a pentacyclic triterpene which is believe to be the active ingredient for antiinflammatory activity. Beta boswellic acid has significant antiinflammatory activity in acute inflammation models in animals using carageenan induced paw edema an also in chronic rheumatoid arthritis (Singh et al; Indian Journal of Pharmacy, 1984 16, 51–53). It reduces triidothyronine levels in acute and chronic inflammation. In chronic conditions the acid increases thyroxine levels. It reduces both the volume and leucocyte population in pleural exudate. Sallai Guggul gives short time benefits to arthritis patients by reducing pain and inflammation without any ulcerogenic or other severe side effects (Pachanda et al; Indian Journal of Pharmacy 1981, 15, 65–67).

Turmeric (*Curcuma longa*) (Zingereraceae)

Turmeric or Haldi in Hindi is used very widely as medicine as well as very common ingredient in Indian cooking. The rhizome of turmeric is used in medicines and food as a fine powder.

Significant antiinflammatory activity comparable with phenylbutazone and hydrocortisone was observed by Arora et.al. (Indian Journal of Medical Research 1971, 59, 1289–1291) A volatile oil obtained from turmeric was comparable with cortisone acetate against adjuvant arthritis. Activation of adrenohypophyseal axis by oil is considered to be responsible for late arthritic changes observed by Chandra & Gupta.( Indian Journal of Medical Research 1972, 60, 158–140) Curcumin an alkaloid (differnloyl methane) isolated from the alcoholic extract of turmeric has been shown to be potent antiinflammatory agent and is considered to be its active ingredient. Naturally occurring analogues of curcumin from turmeric were screened for antiinflammatory activity against carageenan-induced paw edema and were compared with phenylbutozone. Curcumin analogues revealed a dose dependent effect and its action was similar to NSAIDs. A clinical trial on anti rheumatic activity of curcumin was evaluated by Deodhar et al. (Indian Journal of Medical Research, 1980, 71, 632–634) on a short term double blind, cross over study. Morning stiffness, walking time and swelling were significantly improved as compared to baseline readings. Further work on antiinflammatory and antiarthritic activity has also been carried out by Thatte et. al. (Indian Journal of Pharmacology 1986, 18 (1), 19–21) Curcumin has also been found to have beneficial effect on vascular prostaglandin synthesis. (Srivastava et al Arzheim. Forsch. (Drug Research); 1986 36(i) (9) 715). Thus, Turmeric (*Curcuma longa*) natural plant is in the form of a rhizome. The powder of Turmeric (*Curcuma longa*) contains the alkaloid curcumin which is considered to be the active compound. The powder as well as the volatile oil has antiinflammatory properties. Curcumin has effects like NSAIDS. Turmeric (*Curcuma longa*) has significant antiinflammatory activity both in acute and chronic models. It has mild antiseptic activity. Clinically, it was found to improve stiffness of joints, morning stiffness walking time, joint swelling and the like. It has beneficial effects on vascular prostaglandin synthesis. Thus given alone Turmeric has limited benefits in rheumatoid arthritis. The therapeutic dose for optimal activity if used alone is in the range of 5 to 10 grammes of dry powder daily. This can produce a feeling a nausea.

Ginger (*Zingiber officinale*)

Ginger (*Zingiber officinale*) gives relief from muscular discomfort and pain. It inhibits prostaglandin and leukotriene biosynthesis and histamine release. Thus it acts as an antiflammatory as well as an antacid agent. It is a dual inhibitor of the lipoxigenase and cycloxigenase system. Ginger contains 1–4% essential oil (oleoresin). During the last 45 years many chemical investigations have been carried out on the constituents of the essential oil. All together more than 200 different volatiles have been identified in essential oil wherein the pharmacological activity is confined. The essential oil contains mixture of various terpenes as well as some other non-terpenoid compounds. Due to the large battery of compounds belonging to various chemical classes, it is likely that crude ginger powder intake brings about amelioration of symptoms by interfering with the production and release of products of lipid membranes (eicosanoids, reactive oxygen), peptides and proteins (lysosomal enzymes, growth factors, lymphokines, bradykinin), amino acids (histamin, serotonin) etc. (Kiuchi F. et al; Chemical and Pharmaceutical Bulletin, 1982, 30, 747–754). Although this is mostly speculative, the experimental data and observations suggest that ginger inhibits both the cyclooxygenase and lypoxygenase products, i.e. it can be a dual inhibitor of eicosanoid synthesis (Srivastava and Mustafa; Medical Hypotheses; 1992; 39 342–348).

Non-steroidal anti-inflammatory drugs have three major actions, all of which are related to inhibition of cyclooxygenase resulting in decreased formation of prostanoids. Firstly, an anti-inflammatory action achieved by reduced production of vasodilator prostaglandins (PGE2, PGI2) which means less vasodilation and, indirectly less oedema. Secondly, an analgesic effect achieved by reduced prostaglandin production (less sensitization of nociceptic nerve endings to the inflammatory mediators bradykinin and 5-hydroxytryptamine). Thirdly, an antipyretic effect which is probably due to a decrease in the mediator PGE2 generated in response to inflammatory pyrogens, much as interleukin-1. Since ginger inhibits prostanoid synthesis and also products of 5-lipoxygenase, its ameliorative effects in arthritis and muscular discomforts could be related to reduced formation of prostanoids and leukotrienes. Because of such a possibility a decrease in the carageenan-induced oedema formation in the rat's paw after 3 g of ginger extract administration has been demonstrated and the potency of the extract in the acute inflammation test appears to be comparable to that exhibited by acetyl salicylic acid reported in the same study. (Mascolo N. et al Journal of Ethnopharmocology 1989, 27, 129–140).

One of the features of inflammation is increased oxygenation of arachidonic acid which is metabolized by two enzymic pathways—the cyclooxygenase (CO) and the 5-lipoxygenase (5-LO)-leading to the production of prostaglandins and leukotrienes respectively. Amongst the CO products, PGE2 and amongst the 5-LO products, LTB4 are considered important mediators of inflammation. More than 200 potential drugs ranging from non-steroidal anti-inflammatory drugs, corticosteroids, gold salts, disease modifying anti-rheumatic drugs, methotrexate, cyclosporine are being tested. None of the drugs has been found safe; all are known to produce from mild to serious side-effects. Ginger is described in Ayurvedic and Tibb systems of medicine to be useful in inflammation and rheumatism. In all 56 patients (28 with rheumatoid arthritis, 18 with osteoarthritis and 10 with muscular discomfort) used powdered ginger against their afflictions. Amongst the arthritis patients more than three-quarters experienced, to varying degrees, relief in pain and swelling. All the patients with muscular discomfort experienced relief in pain. None of the patients reported adverse effects during the period of ginger consumption which ranged from 3 months to 2.5 years.(Srivastava and Mustafa; 1992 ibid) It is suggested that at least one of the mechanisms by which ginger shows its ameliorative effects could be related to inhibition of prostaglandin and leukotriene biosynthesis, i.e. it works as a dual inhibitor of eicosanoid biosynthesis. Used alone fresh Ginger is required to be used in substantially high doses (50 grammes daily), which is not only inconvenient but can act as an irritant to the gastric mucosa. In dry form for any significant results 7 to 10 grammes of dry ginger powder has to be taken daily. These therapeutic doses of ginger are extremely inconvenient for the patient and affect patient compliance on a daily basis. Further it has no satisfactorily demonstrated immunomodulatory activity to achieve long term benefits in the controlling the progress of degeneration.

Kulkarni R. R. et al (Indian Journal of Pharmacology 1992, 24, 98–101) reported the moderate clinical efficacy of a formulation containing Ashwagandha, Salai Guggul, Turmeric along with a complex salt of Zinc (Jasad Bhasma) of unknown structure, prepared in accordance with Ayurvedic principles (Sharangdhar Samhita Translated by K. K. S. Moorthy, 1984). This formulation was developed by this inventor in 1988. In this formulation commercially marketed under the brand name "Articulin forte", the Ashwagandha, Salai Guggul and Turmeric were used in their crude forms. Further the dosages required for optimal therapeutic activity were in the range of 6 to 7.5 graammes of the composition per day. 20 patients having varied symptoms of Rheumatoid Arthritis such as morning stiffness, joint swelling and tenderness, disability and/or loss of function due to joint deformity and serlogically positive Rheumatoid factor (RF), were placed on the formulation for a period of three months. There was clinical improvement in a significant number of cases. However, only 9 patients showed changes in qualitative test to presence of RF. Radiological assessment did not show any reversal of the degeneration process.

Further work by this inventor on the formulation detailed above led to identification of various practical and therapeutic problems in order to achieve optimal efficacy, such as poor patient compliance because of inconvenient dosage pattern, reversal of benefits after discontinuation of the therapy, technological problems in maintaining desired quality in the suitable dosage form. Further the above formulation was not able to produce quick analgesic and antiinflammatory activity because of the sub therapeutic doses of the ingredients and lack of a potential agent which could inhibit both the cyclooxygenase and lipoxygenase pathways. To sum up, the above formulation had inherent deficiencies and therefore could not give a well controllable and reporducible short term and long term benefits to the patients.

OBJECTS OF THE PRESENT INVENTION

It is an object of the invention to provide a composition based on plant extracts that has potential immunomodulatory activity along with other supportive activity for providing short and long term benefits to patients having immunopathological disorders such as rheumatic diseases, and degenerative diseases of the musculoskeletal system, such as osteoarthritis.

A further object of this invention is to provide a composition aforesaid that acts without exerting toxic or side effects.

Still another object of this invention is to provide a disease-specific synergistic composition, in convenient dosage form.

It is another object of the invention to produce beneficiated plant extracts from the following plants ASHWAGANDHA (*Withania somnifera*), SALLAI GUGGUL (*Boswellia serrata*) TURMERIC (*Curcuma longa*), and GINGER (*Zingiber officinale*).

Another object of the present invention is to provide methods for the preparation of plant extracts useful in the treatment of rheumatic diseases, immunodeficiency diseases and various forms of degenerative musculoskeletal diseases such as rheumatoid arthritis and osteoarthritis.

A further object of the invention is to provide a method of treatment of rheumatic diseases, immunodeficiency diseases and various forms of degenerative musculoskeletal diseases such as rheumatoid arthritis and osteoarthritis, in a method which, unlike present available treatment which usually have severe side effects, demonstrates little in the way of side effects.

SUMMARY OF THE INVENTION

According to this invention there is provided a method of treating degenerative musculoskeletal diseases such as rheumatoid arthritis and osteoarthritis in an animal, typically a human., comprising administering to the animal, typically enterally, in a convenient dosage form, a therapeutically effective amount of the beneficiated extracts of the plants ASHWAGANDHA (*Withania somnifera*), SALLAI GUGGUL (*Boswellia serrata*), TURMERIC (*Curcuma longa*), and GINGER (*Zingiber officinale*) in a predetermined proportion relative to each other with or without other biologically active inorganic ingredients, such as zinc sulphate, the beneficiated plant extracts made in accordance with a novel process which is hereinafter disclosed.

DETAILED DESCRIPTION

Figure 1:
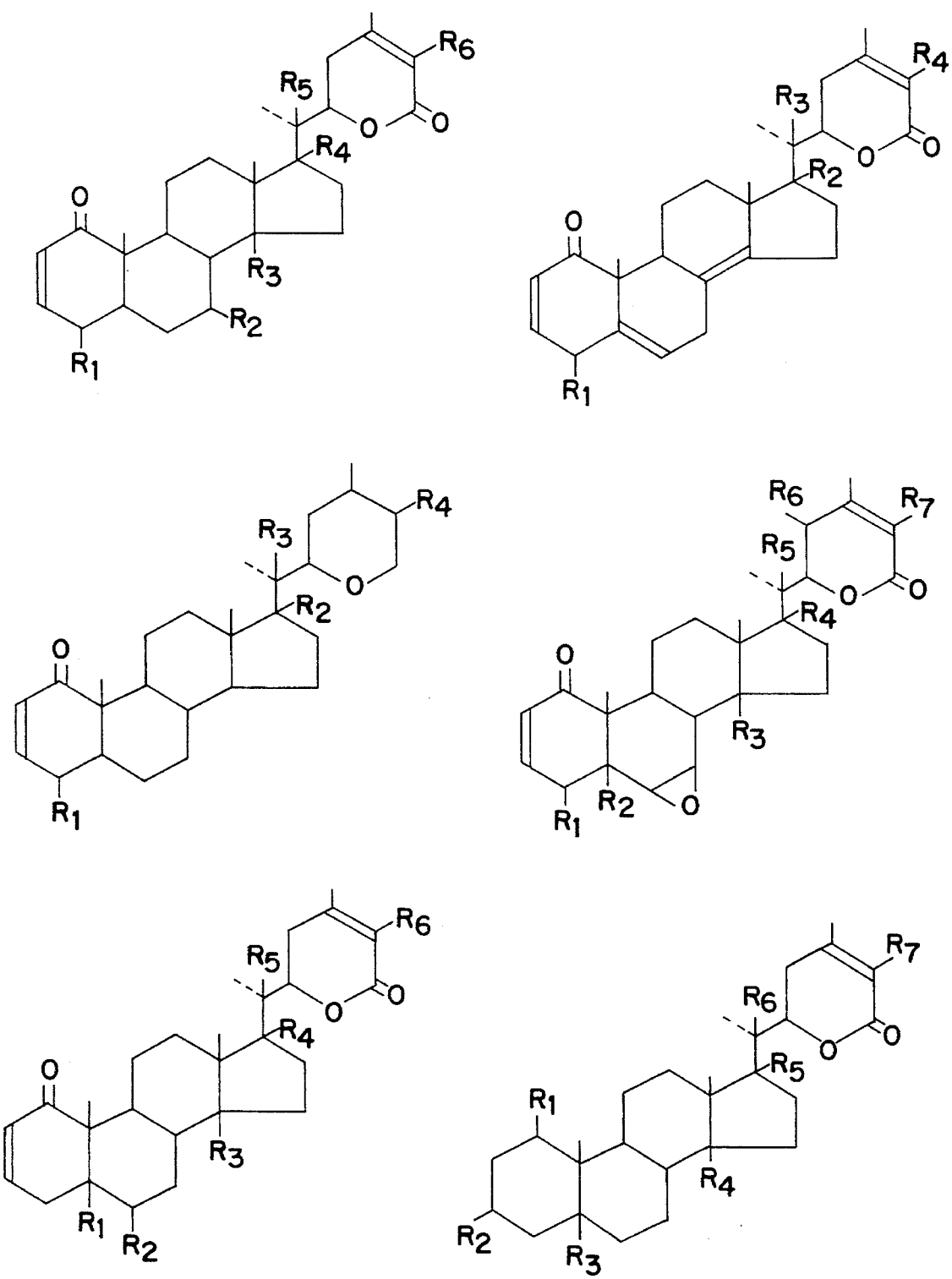
FIG. 1 of the drawing illustrates the structures of Withanolides and Sitoindosides found in ASHWAGANDHA (*Withania somnifera*) wherein R, R1 and R2 stand for an H or an OH radical; R3 for a methyl group, R4 a hydroxymethyl group attached to a sugar moiety and R5, R6 and R7 could be a methyl group, an H or OH radical or a hydroxymethyl group.

The invention provides a method of treating degenerative musculoskeletal diseases such as rheumatoid arthritis and osteoarthritis in an animal, typically a human, comprising administering to the animal, typically enterally, in a convenient dosage form, a therapeutically effective amount of the beneficiated extracts of the plants ASHWAGANDHA (*Withania somnifera*) SALLAI GUGGUL (*Boswellia serrata*), TURMERIC (*Curcuma longa*), and GINGER (*Zingiber officinale*) in a predetermined proportion relative to each other with or without other biologically active inorganic ingredients, such as zinc sulphate, the beneficiated plant extracts made in accordance with a novel process which is hereinafter disclosed.

The novel process comprises, generally, the steps of cleaning the plant from which the pharmacologically or biologically active plant extract has to be obtained to remove any foreign matter thereon;

particulating the plant to obtain a particulated mass having particle size ranging from 0,001 to about 10 mm3;

subjecting the particulated mass to at least one polar and at least one non polar solvent to obtain separate fractions of the plant extract soluble in the respective solvents and mixing the fraction so obtained to obtain the beneficiated plant extract in accordance with this invention.

For instance, in the case of Ashwagandha, the novel process comprises the steps of cleaning the roots of ASHWAGANDHA (*Withania somnifera*) to remove any foreign matter thereon;

particulating the roots to obtain a particulated mass having particle size ranging from 0,001 to about 10 mm3;

subjecting the particulated mass to distillation to obtain a volatile fraction, if any, from the particulated mass;

cooking the steam-treated particulated mass in a polar solvent, such as water to dissolve polar solvent soluble material in the distillation-treated particulated mass to obtain a first solution and a first residue;

filtering the first solution from the first residue;

evaporating the filtrate obtained from the first solution to remove the solvent and obtain a solute designated as fraction A from the particulated mass;

subjecting the first residue to treatment with a second polar solvent such as 75% to 95% ethanol for twelve to thirty-six hours to obtain a second solution and a second residue;

filtering the second solution from the second residue to obtain a second filtrate;

evaporating the second filtrate to remove its solvent and obtain a solute designated as fraction B from the particulated mass;

subjecting the second residue to less polar or nonpolar solvents;

such as petroleum ether, for twelve to thirty-six hours to obtain a third solution and a third residue filtering the third solution from the third residue to obtain a third filtrate;

evaporating the third filtrate to remove its solvent and obtain a solute designated as fraction C from the particulated mass; and homogeneously mixing the volatile fraction, with fractions A, B and C from the particulated mass to obtain a beneficiated plant extract.

The process is suitable for the preparation of a pharmacologically or biologically active plant extract substantially as it occurs in its natural state in a convenient administrable dosage form of any of the plants mentioned hereintofore, namely: ASHWAGANDHA (*Withania somnifera*), SALLAI GUGGUL (*Boswellia serrata*) TURMERIC (*Curcuma longa*), GINGER (*Zingiber officinale*).

The term beneficiated plant extract appearing hereinafter is deemed to mean a plant extract made according to the process enunciated above.

Figure 2:
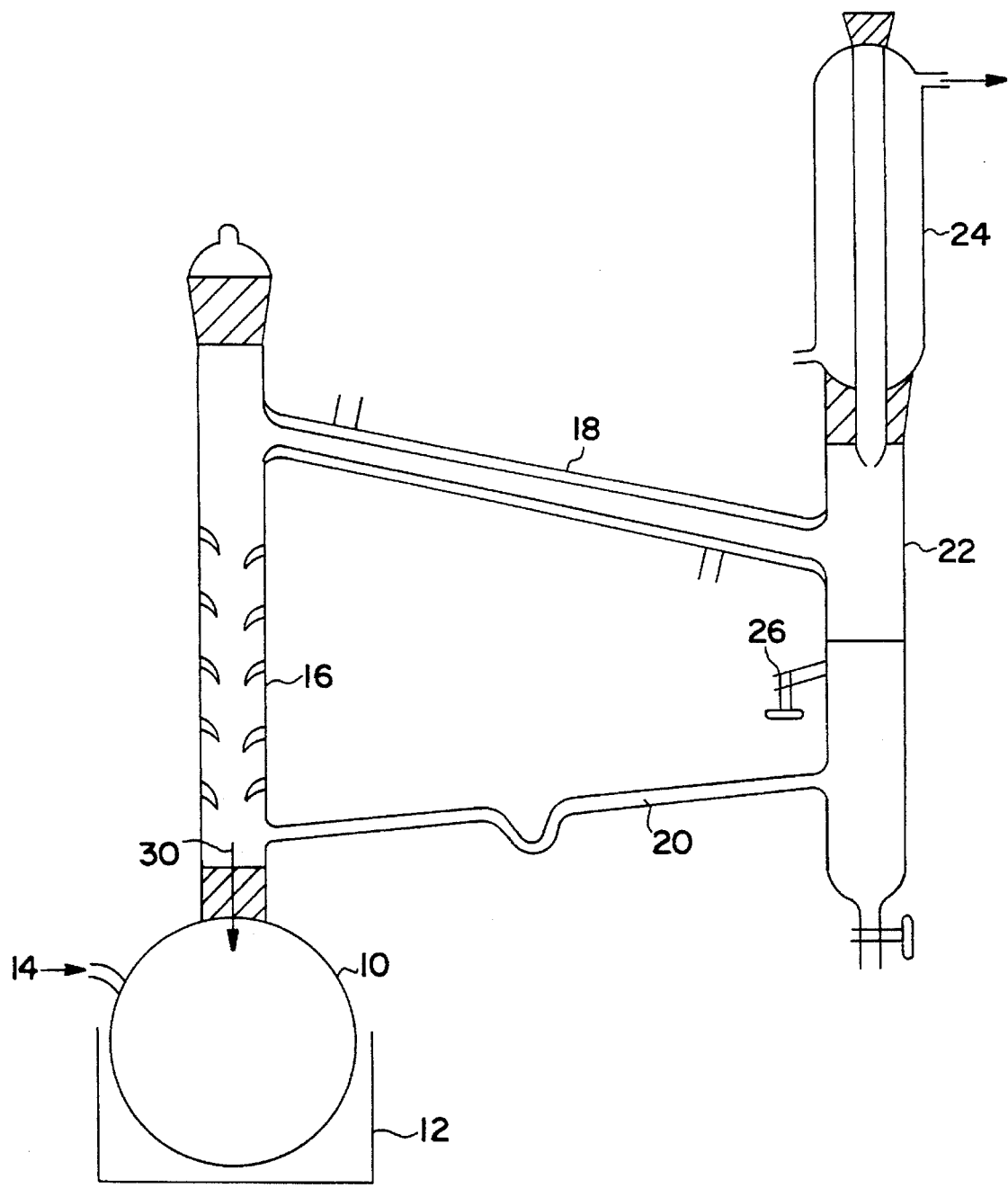
FIGS. 2 & 3 illustrate typical apparatii required for carrying out the process in accordance with one aspect of this invention.
Figure 3:
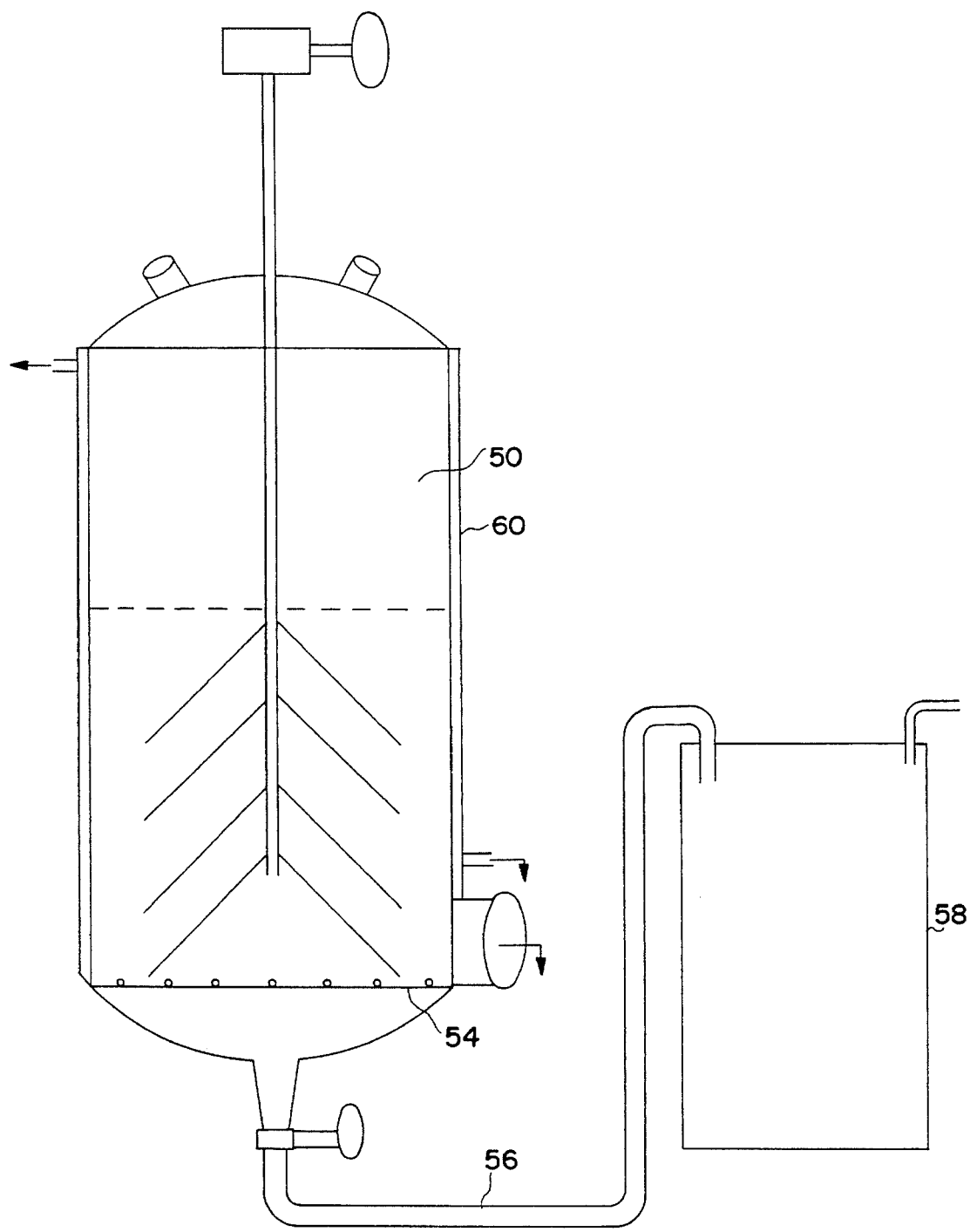

The apparatii shown in FIGS. 2 and 3 can be conveniently used for carrying out the process for obtaining a beneficiated plant extract.

The cleaning of the plant from which the pharmacologically or biologically active plant extract has to be obtained is done to remove any foreign matter thereon. This cleaning can be achieved by manually separating the dirt and other foreign matter adhered to the plant and repeatedly washing the plant with water at room temperature.

The cleaned plant is then particulated in a pulverizer to obtain a particulated mass having particle size ranging from 0,001 to about 10 mm3, typically in the region of 1 mm.

The particulated mass is then subjected to steam distillation to obtain a volatile fraction, if any, from the particulated mass. The apparatus illustrated in FIG. 2 can be conveniently used for carrying out the steam distillation and comprises a flask 10 which is imbedded in a heating source 12. The particulated plant material is introduced into the flask 10 along with water through the opening 30. The flask 10 has an inlet 14 for introducing steam and is fitted with a condenser 16 which has two outlet pipes 18 and 20 which connect the flask 10 to a glass column 22. The pipe 18 is used for sending the mixture of steam and volatile portion to the glass column 22 and the outlet pipe 20 for recycling the water from the reaction flask 10 to the glass column 22 and back. The glass column 22 is fitted with a condenser 24 which condenses the steam and volatile portion received from the flask into the glass column 22. The glass column 22 has a tap 26 located between the inlet portion of the two pipes 18 and 22 for collecting the volatile oil fraction from the plant extract introduced in the reaction flask 10.

The steam treated plant extract and the water collected from the apparatus of FIG. 1 is led to the extraction chamber 50 of FIG. 2, which is provided with a stirrer 52 and a filtering element 54 at its base. In the process of steam distillation as described above, the plant material is also cooked and the water soluble elements in the particulated plant material get dissolved in the water and are led away from the extraction chamber 50 via the outlet pipe 56 to an evaporator chamber 58 in which the water is evaporated to leave the water soluble residue in the evaporator chamber 58. As seen in FIG. 3 the extraction chamber is provided with a steam jacket 60, if required, to maintain the temperature of the internal environment of the chamber 50. The particulated mass in the extraction chamber 50 is treated with further hot/cold water to remove any residuary water soluble material. The residue obtained in the evaporator chamber after repeated water treatment is fraction A. The evaporator chamber surface is scrapped to remove all traces of this residue.

The particulated plant mass in the extraction chamber 50 is then subjected to treatment with 75% to 95% ethanol for twelve to thirty-six hours. The solution obtained in the extraction chamber 50 is then filtered through to the evaporator chamber 58 and the residue (Fraction B) is collected in a similar fashion as for the Fraction A.

The particulated plant mass in the extraction chamber 50 is then subjected to treatment with a non polar solvent such as petroleum ether for twelve to thirty-six hours. The solution obtained in the extraction chamber 50 is then filtered through to the evaporator chamber 58 and the residue (Fraction C) is collected in a similar fashion as for the Fractions A and B. The volatile fraction is mixed with fractions A, B and C to obtain the beneficiated plant extract in accordance with this invention.

Example 1

Preparation of beneficiated extract of the plant Ashwagandha: The roots of Ashwagandha duly identified by a botanist were shade dried cleaned and pulverised to a mesh size of 1 to 2 cubic centimeters. The powdered roots (1 kg were transferred into a flask alongwith 5 liters of water which was added through an opening in the flask. Steam was introduced through an inlet while heating the flask externally by heating source in a controlled manner, so that the total volume in the flask did not increase appreciably. A steam volatile fraction was collected in a condensing column and was removed. Steam distillation was continued until no further oil was formed in the condensing column. The steam volatile fraction obtained weighed 5 gms. The particulated mass left over after steam distillation was transferred to an extraction chamber and water was added to the mass in the extraction chamber. The particulated mass and water was thoroughly stirred for an hour and the liquid content of the mass was filtered through a filtration assembly. The filtrate consisting of water and water extract was led to an evaporation chamber. Fresh water (5 liters) was introduced in the extraction chamber and the entire mass was heated to approximately 50 degree centigrade using steam introduced into the steam jacket around the extraction chamber. The hot mass was stirred for another hour and the liquid content filtered. The filtrate was again transferred to the evaporator. This process was continued 3 times. In the evaporator, water was removed using heat and vacuum and the dried residue weighing about 60 gms was collected from the evaporator by scrapping (fraction A). To the mass remaining in the extraction chamber, 5 liters of ethanol (75–90%) were added and the mixture was stirred for an hour and left stagnant for 36 hours. The liquid content was then filtered and the filtrate was transferred to the evaporator. 3 more additions of ethanol were done to the mass in the extraction chamber and the filtrate was collected in the evaporator each time. Ethanol was removed from the filtrate in the evaporator by vacuum. The residue weighing about 30 gms was left behind which was scrapped from the evaporator and preserved (fraction B). To the residual particulated mass in the extraction chamber, 5 liters of petroleum ether (60 to 80%) were introduced and left for 36 hours. The liquid portion was filtered and the filtrate was transferred to the evaporator. The treatment with petroleum ether was repeated 3 times and all the filtrates were collected in the evaporator. The petroleum ether was removed under vacuum. The residue in the evaporator was scrapped and stored and weighed 5 gms (fraction C). The volatile fraction (5 gms), fraction A (60 gms), fraction B (30 gms) and fraction C (5 gms) were thoroughly mixed using a blender. Thus a total mass of approximately 100 gms of Ashwagandha beneficiated extract was obtained from 1 kg of root powder which was stored below 10 degrees.

Example 2

Preparation of beneficiated extract of the plant Sallai Guggul: The gum extrudate of the plant Sallai Guggul duly identified by a botanist was cleaned to remove foreign particles. The dried gum was particulated to a mesh size of 1 to 2 mm. The gum (1 kg) was transferred into a flask along with 5 liters of water which was added through an opening in the flask. Steam was introduced through an inlet while heating the flask externally by heating source in a controlled manner, so that the total volume in the flask did not increase appreciably. A steam volatile fraction was collected in a condensing column and was removed. Steam distillation was continued until no further oil was formed in the condensing column. The steam volatile fraction obtained weighed 90 gms. The mass left over after steam distillation was transferred to an extraction chamber and water was added to the mass in the extraction chamber. The mass and water was thoroughly stirred for an hour and the liquid content of the mass was filtered through a filtration assembly. The filtrate consisting of water and water extract was led to an evaporation chamber. Fresh water (5 liters) was introduced in the extraction chamber and the entire mass was heated to approximately 50 degree centigrade using steam introduced into the steam jacket around the extraction chamber. The hot mass was stirred for another hour and the liquid content filtered. The filtrate was again transferred to the evaporator. This process was continued 3 times. In the evaporator, water was removed using heat and vacuum and the dried residue weighing about 150 gms was collected from the evaporator by scrapping (fraction A). To the mass remaining in the extraction chamber, 5 liters of acetone (75–90%) were added and the mixture was stirred for an hour and left stagnant for 36 hours. The liquid content was then filtered and the filtrate was transferred to the evaporator. 3 more additions of acetone were done to the mass in the extraction chamber and the filtrate was collected in the evaporator each time. Acetone was removed from the filtrate in the evaporator by vacuum. The residue weighing about 180 gms was left behind which was scrapped from the evaporator and preserved (fraction B). To the residual mass in the extraction chamber, 5 liters of petroleum ether (60 to 80%) were introduced and left for 36 hours. The liquid portion was filtered and the filtrate was transferred to the evaporator. The treatment with petroleum ether was repeated 3 times and all the filtrates were collected in the evaporator. The petroleum ether was removed under vacuum. The residue in the evaporator was scrapped and stored and weighed 30 gms (fraction C). The volatile fraction (90 gms), fraction A (150 gms), fraction B (180 gms) and fraction C (30 gms) were thoroughly mixed using a blender.

Thus a total mass of approximately 450 gms of Sallai Guggul beneficiated extract was obtained from 1 kg of gum extracted which was stored below 10 degrees.

Example 3

Preparation of beneficiated extract of the plant Turmeric: The rhizomes of Turmeric were shade dried cleaned and pulverised to a mesh size of 1 to 2 cubic millimeters. The Turmeric powder (1 kg) was transferred into a flask alongwith 5 liters of water which was added through an opening in the flask. Steam was introduced through an inlet while heating the flask externally by heating source in a controlled manner, so that the total volume in the flask did not increase appreciably. A steam volatile fraction was collected in a condensing column and was removed. Steam distillation was continued until no further oil was formed in the condensing column. The steam volatile fraction obtained weighed 20 gms. The particulated mass left over after steam distillation was transferred to an extraction chamber and water was added to the mass in the extraction chamber. The particulated mass and water was thoroughly stirred for an hour and the liquid content of the mass was filtered through a filtration assembly. The filtrate consisting of water and water extract was led to an evaporation chamber. Fresh water (5 liters) was introduced in the extraction chamber and the entire mass was heated to approximately 50 degree centigrade using steam introduced into the steam jacket around the extraction chamber. The hot mass was stirred for another hour and the liquid content filtered. The filtrate was again transferred to the evaporator. This process was continued 3 times. In the evaporator, water was removed using heat and vacuum and the dried residue weighing about 30 gms was collected from the evaporator by scrapping (fraction A). To the mass remaining in the extraction chamber, 5 liters of ethanol (75–90%) were added and the mixture was stirred for an hour and left stagnant for 36 hours. The liquid content was then filtered and the filtrate was transferred to the evaporator. 3 more additions of ethanol were done to the mass in the extraction chamber and the filtrate was collected in the evaporator each time. Ethanol was removed from the filtrate in the evaporator by vacuum. The residue weighing about 40 gms was left behind which was scrapped from the evaporator and preserved (fraction B). To the residual particulated mass in the extraction chamber, 5 liters of petroleum ether (60 to 80%) were introduced and left for 36 hours. The liquid portion was filtered and the filtrate was transferred to the evaporator. The treatment with petroleum ether was repeated 3 times and all the filtrates were collected in the evaporator. The petroleum ether was removed under vacuum. The residue in the evaporator was scrapped and stored and weighed 10 gms (fraction C). The volatile fraction (20 gms), fraction A (30 gms), fraction B (40 gms) and fraction C (10 gms) were thoroughly mixed using a blender. Thus a total mass of approximately 100 gms of Ashwagandha beneficiated extract was obtained from 1 kg of rhizome ponder which was stored below 10 degrees.

Example 4

Preparation of beneficiated extract of the plant Ginger: The rhizomes of Ginger were shade dried cleaned and pulverised to a mesh size of 1 to 2 cubic millimeters. The Ginger powder (1 kg) was transferred into a flask alongwith 5 liters of water which was added through an opening in the flask. Steam was introduced through an inlet while heating the flask externally by heating source in a controlled manner, so that the total volume in the flask did not increase appreciably. A steam volatile fraction was collected in a condensing column and was removed. Steam distillation was continued until no further oil was formed in the condensing column. The steam volatile fraction obtained weighed 25 gms. The particulated mass left over after steam distillation was transferred to an extraction chamber and water was added to the mass in the extraction chamber. The particulated mass and water was thoroughly stirred for an hour and the liquid content of the mass was filtered through a filtration assembly. The filtrate consisting of water and water extract was led to an evaporation chamber. Fresh water (5 liters) was introduced in the extraction chamber and the entire mass was heated to approximately 50 degree centigrade using steam introduced into the steam jacket around the extraction chamber. The hot mass was stirred for another hour and the liquid content filtered. The filtrate was again transferred to the evaporator. This process was continued 3 times. In the evaporator, water was removed using heat and vacuum and the dried residue weighing about 125 gms was collected from the evaporator by scrapping (fraction A). To the mass remaining in the extraction chamber, 5 liters of acetone (75–90%)were added and the mixture was stirred for an hour and left stagnant for 36 hours. The liquid content was then filtered and the filtrate was transferred to the evaporator. 3 more additions of acetone were done to the mass in the extraction chamber and the filtrate was collected in the evaporator each time. Acetone was removed from the filtrate in the evaporator by vacuum. The residue weighing about 90 gms was left behind which was scrapped from the evaporator and preserved (fraction B). To the residual particulated mass in the extraction chamber, 5 liters of petroleum ether (60 to 80%) were introduced and left for 36 hours. The liquid portion was filtered and the filtrate was transferred to the evaporator. The treatment with petroleum ether was repeated 3 times and all the filtrates were collected in the evaporator. The petroleum ether was removed under vacuum. The residue in the evaporator was scrapped and stored and weighed 10 gms (fraction C). The volatile fraction (25 gms), fraction A (125 gms), fraction B (90 gms) and fraction C (10 gms) were thoroughly mixed using a blender. Thus a total mass of approximately 250 gms of Ginger beneficiated extract was obtained from 1 kg of rhizome powder which was stored below 10 degrees. It is suggested that the beneficiated extracts of correctly selected plants, in accordance with this invention, when mixed in the proper proportions in suitable dosage form will have a synergistic effect and such formulations will address most of the requirements of an ideal antirheumatic drug. These therapeutic requirements include: analgesic activity, antiinflammatory activity for symptomatic relief; immunomodulatory activity to correct the underlying immunopathological process, to control the progress of the disease, anabolic activity to counteract the degenerative changes to protect further damage and morbidity.

The synergistic combination of the beneficiated plant extracts of the following plants are suitable for the treatment of rheumatoid arthritis:

ASHWAGANDHA (*Withania somnifera*), SALLAI GUGGUL (*Boswellia Serrata*) TURMERIC (*Curcuma longa*), GINGER (*Zingiber officinale*).

The proportion of these beneficiated plant extracts in a formulation and a selected suitable dosage form either in tablet or capsule form or in liquid oral form will be required to get the maximum advantage for the patients. The formulation can be considered as the minimum required medicine and more ingredients may be added to increase it clinical usefulness. Such additional agents can be nutritional supplements in organic or inorganic form.

Accordingly, for the treatment of musculoskeletal disorders and rheumatic diseases, more precisely for the treatment of Rheumatoid Arthritis and Osteoarthritis there is provided a composition containing a homogeneous mixture of beneficiated extracts of Ashwagandha (*Withania somnifera*) 30 to 50 percent ), Sallai Guggul (*Boswellia serrata*) (30 to 50 percent ), Turmeric (*Curcuma longa*) (Trace to 15 percent) and Ginger (*Zingiber officinale*) (5 to 15 percent).

Typically, the composition according to the invention for the treatment of rheumatic disease contains the following ingredients by mass of active ingredients:

Ashwagandha (*Withania somnifera*) 40.5 percent Sallai Guggul (*Boswellia serrata*) ) 40.5 percent Turmeric (*Curcuma longs*) 8.2 percent; and Ginger (*Zingiber officinale*) 10.8 percent, In accordance with the preferred method of administration the dosage of mass of active ingredients is 4 to 10 mg/kg of body mass of an individual/per day and preferably 6 mg/kg of body mass of the individual/per day, A 792 mg tablet was prepared using 74 mgs of beneficiated plant extracts containing 30 mgs of Ashwagandha beneficiated extract, 30 mgs of Sallai Guggul beneficiated extract, 6 mgs of Turmeric beneficiated extract and 8 mgs of Ginger beneficiated extract. To this extract was added 50 mgs of Zinc Sulphate and 668 mgs of excipients mainly di calcium phosphate.

Zinc is known to be intimately involved in the metabolism of various biological systems ranging from collagen, bone metabolism, complement system, macrophage function and the like. Zinc also has anti inflammatory activity and it participates in the etiopathogenesis of rheumatoid arthritis whereever zinc has been found to be deficient. Zinc supplementation has been found to be beneficial. (Medoms et al, Brityish Medical Journal, 1983, 287, 113).

The recommended dose is 6 tablets a day in 3 divided doses for a period of not less than three months.

The aforesaid formulation when tested in animals showed a mild analgesic, antiinflammatory activity and also antiarthritic activity in in vivo chronic models like cotton pellet granuloma, adjuvant induced arthritis and the like and also in acute models like carrageenan or 48\80 induced paw edema. When given to patients of rheumatoid arthritis it reduced the Ritche Articular index, joint score, severity of pain, morning stiffness and improve overall clinical picture of the patient with increases in grip strength. Among the biochemical parameters the composition reduced elevated ESR, serum concentration of acute phase proteins, and C-reactive protein. The composition also showed general beneficial effects on parameters like plasma viscosity, total serum sulfhydryl and other laboratory variables, rheumatoid factor which is a more specific immunological variable to monitor and in tests conducted on patients, the composition removed rheumatoid factor from the serum in moderate proportions of seropositive arthritis patients and 30–50% of these patients received considerable long protection against degenerative and destructive processes which commonly occur in such diseases resulting in morbidity. The composition in long-term treatment of minimum six months duration also showed beneficial radiological changes. Minimum duration of treatment with the composition for considerable clinical benefits is three months and dose will be six tablets or capsules or equivalent quantity of oral liquid three times a day preferably after food intake. It is also advised to reduce consumption of sour and fermented foods such as yoghurt. It is also advised that the patient should ensure consumption of the required daily intake of nutrients such as iron, calcium and Vitamin C.

Case Studies

A 55 year old female patient complaining of severe knee joint pain was treated with the aforesaid composition in a daily basis for two months with the following results: The parameter specifies the condition of the patient at the time of entrring the therapy program and at the time of exiting therefrom

| parameter | entry | exit |
|---|---|---|
| Rheumatoid factor | + | − |
| severity of pain | 4 | 2 |
| morning stifness (in minutes) | 40 | 20 |
| joint score | 4 | 3 |
| Ritche Articular index | 4 | 2 |
| Grip strength | 20 | 40 |
| ESR | 40 | 22 |

A 48 year old female patient complaining of severe wrist joint pain was treated with the aforesaid composition in a daily basis for one month with the following results: The parameter specifies the condition of the patient at the time of entrring the therapy program and at the time of exiting therefrom

| parameter | entry | exit |
|---|---|---|
| Rheumatoid factor | + | − |
| severity of pain | 6 | 2 |
| morning stifness (in minutes) | 40 | 22 |
| joint score | 3 | 2 |
| Ritche Articular index | 3 | 1 |
| Grip strength | 10 | 30 |
| ESR | 50 | 20 |
| Disability score | 2 | 0 |

The ingredients of the composition have overlapping activity required for an antirheumatic\antiarthritic drug and they act together synergistically when added in the particular proportion suggested in accordance with the invention. Studies by the inventor have shown that the beneficiated extracts of the various plants disclosed above exhibit biological activity far greater than the corresponding quantity of crude powder from which the beneficiated extract is derived. For instance, 30 mg of Ashwagandha (*Withania somnifera*) extract, obtained from 300 mgs of crude powder, provides the equivalent pharmacological and biological activity corresponding to 1000 mgs of crude powder; 30 mgs of Sallai Guggul extract (*Boswellia serrata*), obtained from 66 mgs of crude powder, provides the equivalent pharmacological and biological activity corresponding to 200 mg of crude powder; and similarly the activity equivalence of 6 gms of turmeric beneficiated extract, obtained from 60 mgs, is 200 mgs of crude powder, and 8 mgs of Ginger beneficiated extract, obtained from 32 mgs of crude powder, is 100 mgs of crude powder.

The probable reason for this increase in activity in the beneficiated extract is that a significant portion of active ingredients found in the crude powder is not absorbed in the body and is eliminated along with the cellulosic, fibrous or other non digestible material found in the crude powder when the crude powder is consumed in the unbeneficated form. The process disclosed in accordance with this invention creates a composition which retains the natural proportions of the active ingredients of a pharmacologically beneficial plant and at the same time provides a convenient dosage formulation. An additional benefit is that, the process of beneficiation makes the consumption of plant extracts economical, since there is a more than three fold increase in the activity equivalence and a lesser quantity of crude powder is required to provide the required therapeutic dosage of a pharmacologically active plant.

I claim:

1. A method of treating degenerative musculoskeletal disease in an animal comprising administering to the animal an amount of a composition containing extracts of 30 to 50% by weight of ASHWAGANDHA (*Withania somnifera*) roots, 30 to 50% by weight of SALLAI GUGGUL (*Boswellia serrata*) gum exudate, trace to 15% by weight of TURMERIC (*Curcuma longa*) rhizomes, and 5 to 15% by weight of GINGER (*Zingiber officinale*) rhizomes, sufficient to treat degenerative musculoskeletal disease, wherein each of the plant part extracts is prepared by first cleaning the plant part to remove any foreign matter; particulating the plant part to obtain a particulated mass having a particle size ranging from 0.001 to 10 mm$^3$; subjecting the particulated mass to distillation to obtain a volatile fraction, if any; cooking the steam-treated particulated mass in a polar solvent, to dissolve polar solvent soluble material to obtain a first solution and a first residue; filtering the first solution from the first residue; evaporating the filtrate obtained from the first solution to remove the solvent and obtain a solute designated as fraction A from the particulated mass; subjecting the first residue to treatment with a second polar solvent, for twelve to thirty-six hours to obtain a second solution and a second residue; filtering the second solution from the second residue to obtain a second filtrate; evaporating the second filtrate to remove its solvent and obtain a solute designated as fraction B from the particulated mass; subjecting the second residue to nonpolar solvents for twelve to thirty-six hours to obtain a third solution and a third residue; filtering the third solution from the third residue to obtain a third filtrate; evaporating the third filtrate to remove the solvent and obtain a solute designated as fraction C; and homogeneously mixing the volatile fraction, with fractions A, B, and C, to obtain the plant part extract.

2. The method of claim 1, wherein the administration is enteral.

3. The method of claim 1, in which the administration is at a dosage of 4 to 10 mg/kg of body mass of the animal/per day.

4. The method of claim 3 wherein the dosage is about 6 mg/kg of body mass of the animal per day.

5. The method of claim 1, wherein the animal is human.

6. The method of claim 1, wherein the degenerative musculoskeletal disease is rheumatoid arthritis.

7. The method of claim 1, wherein the degenerative musculoskeletal disease is osteo arthritis.

8. The method of claim 1, which includes the administration of zinc sulphate along with the composition.

9. A composition for treating degenerative musculoskeletal disease comprising an amount of a homogenous mixture of 30 to 50% by weight of extracts of ASHWAGANDHA (*Withania somnifera*) roots, 30 to 50% by weight of extracts of SALLAI GUGGUL (*Boswellia serrata*) gum exudate, trace to 15% by weight of extracts of TURMERIC (*Curcuma longa*) rhizomes, and 5 to 15% by weight of extracts of GINGER (*Zingiber officinale*) rhizomes, sufficient to treat degenerative musculoskeletal disease, and an inert pharmaceutical carrier, wherein each of the plant part extracts is prepared by first cleaning the plant part to remove any foreign matter; particulating the part to obtain a particulated mass having a particle size ranging from 0.001 to 10 mm$^3$; subjecting the particulated mass to distillation to obtain a volatile fraction, if any; cooking the steam-treated particulated mass in a polar solvent, to dissolve polar solvent soluble material to obtain a first solution and a first residue; filtering the first solution from the first residue; evaporating the filtrate obtained from the first solution to remove the solvent and obtain a solute designated as fraction A from the particulated mass; subjecting the first residue to treatment with a second polar solvent, for twelve to thirty-six hours to obtain a second solution and a second residue; filtering the second solution from the second residue to obtain a second filtrate; evaporating the second filtrate to remove its solvent and obtain a solute designated as fraction B from the particulated mass; subjecting the second residue to nonpolar solvents for twelve to thirty-six hours to obtain a third solution and a third residue; filtering the third solution from the third residue to obtain a third filtrate; evaporating the third filtrate to remove the solvent and obtain a solute designated as fraction C; and homogeneously mixing the volatile fraction, with fractions A, B, and C, to obtain the plant part extract.

10. A composition of claim 9 also containing a zinc salt.

11. A pharmaceutical composition as claimed in claim 10 which is a mixture of 74 mgs of extracts containing 30 mgs of an extract of ASHWAGANDHAA (*Withania somnifera*), 30 mgs of an extract of extracts of SALLAI GUGGUL (*Boswellia serrata*), 6 mgs of an extract of TURMERIC (*Curcuma longa*) and 8 mgs of an extract of GINGER (*Zingiber officinale*), 50 mgs of Zinc Sulfate and 668 mgs of di-calcium phosphate.

12. A pharmaceutical composition as claimed in claim 9, containing a homogeneous mixture of Ashwagandha (*Withania somnifera*) 40.5 percent, Sallai Guggul (*Boswellia serrata*)) 40.5 percent, Turmeric (*Curcuma longa*) 8.2 percent; and Ginger (*Zingiber officinales*) 10.8 percent of the mass of active ingredient.

* * * * *